United States Patent
Howard et al.

(10) Patent No.: US 9,402,993 B2
(45) Date of Patent: Aug. 2, 2016

(54) SYSTEMS AND METHODS FOR ENHANCING PADDLE LEAD PLACEMENT

(75) Inventors: Joshua Dale Howard, Granada Hills, CA (US); Anne Margaret Pianca, Santa Monica, CA (US); Aditya Vasudeo Pandit, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 850 days.

(21) Appl. No.: 13/439,077

(22) Filed: Apr. 4, 2012

(65) Prior Publication Data
US 2012/0259396 A1 Oct. 11, 2012

Related U.S. Application Data

(60) Provisional application No. 61/474,115, filed on Apr. 11, 2011.

(51) Int. Cl.
*A61N 1/05* (2006.01)

(52) U.S. Cl.
CPC ............ *A61N 1/0553* (2013.01); *A61N 1/0558* (2013.01)

(58) Field of Classification Search
CPC ... A61N 1/0553; A61N 1/0558; A61N 1/057; A61N 2001/0582; A61N 2001/372; A61B 5/6882–5/6884
USPC .......................................... 607/116, 117, 132
See application file for complete search history.

(56) References Cited

U.S. PATENT DOCUMENTS

| | | |
|---|---|---|
| 5,107,856 A | 4/1992 | Kristiansen |
| 5,746,722 A | 5/1998 | Pohndorf et al. |
| 6,181,969 B1 | 1/2001 | Gord |
| 6,249,707 B1 * | 6/2001 | Kohnen ............. A61B 17/3468 607/117 |
| 6,516,227 B1 | 2/2003 | Meadows et al. |
| 6,587,733 B1 * | 7/2003 | Cross et al. .................... 607/116 |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase |

(Continued)

FOREIGN PATENT DOCUMENTS

| | | |
|---|---|---|
| DE | 3300723 A1 | 7/1984 |
| WO | WO 2005028025 A1 | 3/2005 |

(Continued)

OTHER PUBLICATIONS

International Search Report and Written Opinion for International Patent Application No. PCT/US2012/032196, mailed Jul. 5, 2012.

*Primary Examiner* — Eugene Wu
(74) *Attorney, Agent, or Firm* — Lowe Graham Jones PLLC; Bruce E. Black

(57) ABSTRACT

A paddle lead assembly for providing electrical stimulation of patient tissue includes a paddle body; a plurality of electrodes disposed on the paddle body; a plurality of lead bodies coupled to the paddle body; an array of terminals disposed on each of the plurality of lead bodies; and a plurality of conductive wires. Each conductive wire couples one of the electrodes to at least one terminal of at least one of the terminal arrays. The paddle lead assembly further includes an implantation aid configured and arranged to fit over a portion of at least one of the lead bodies to provide additional stiffness proximal to the paddle body for aiding in implantation of the paddle body into a patient.

19 Claims, 6 Drawing Sheets

(56) References Cited

U.S. PATENT DOCUMENTS

| | | |
|---|---|---|
| 7,437,193 B2 | 10/2008 | Parramon |
| 7,515,968 B2 | 4/2009 | Metzler et al. |
| 7,672,734 B2 | 3/2010 | Anderson |
| 7,761,165 B1 | 7/2010 | He |
| 7,774,072 B2 * | 8/2010 | Gerber ................ 607/116 |
| 7,949,395 B2 | 5/2011 | Kuzma |
| 7,974,706 B2 | 7/2011 | Moffitt |
| 8,175,710 B2 | 5/2012 | He |
| 8,224,450 B2 | 7/2012 | Brase |
| 2003/0204228 A1 * | 10/2003 | Cross et al. ............ 607/116 |
| 2005/0004639 A1 * | 1/2005 | Erickson ............... 607/122 |
| 2005/0165465 A1 | 7/2005 | Pianca |
| 2005/0182470 A1 * | 8/2005 | Cross ................... 607/117 |
| 2005/0288758 A1 * | 12/2005 | Jones et al. ............ 607/116 |
| 2007/0150036 A1 | 6/2007 | Anderson |
| 2008/0306442 A1 * | 12/2008 | Bardsley .......... A61B 17/3421 604/104 |
| 2009/0248111 A1 * | 10/2009 | Pianca et al. ............ 607/46 |
| 2010/0004721 A1 * | 1/2010 | Bryce .............. A61B 17/3468 607/117 |
| 2010/0030227 A1 * | 2/2010 | Kast ................ A61B 17/3468 606/129 |
| 2010/0070010 A1 * | 3/2010 | Simpson ................ 607/117 |
| 2011/0009933 A1 * | 1/2011 | Barker ................. 607/116 |
| 2011/0022142 A1 * | 1/2011 | Barker et al. ........... 607/117 |
| 2011/0230893 A1 * | 9/2011 | Barker .............. A61N 1/0551 606/129 |
| 2011/0319973 A1 * | 12/2011 | Swanson et al. .......... 607/116 |
| 2012/0209285 A1 * | 8/2012 | Barker et al. ........... 606/129 |

FOREIGN PATENT DOCUMENTS

| | | |
|---|---|---|
| WO | WO 2008085528 A1 | 7/2008 |
| WO | WO 2009105646 A1 | 8/2009 |

* cited by examiner

SYSTEMS AND METHODS FOR ENHANCING PADDLE LEAD PLACEMENT

CROSS-REFERENCE TO RELATED APPLICATIONS

This application claims the benefit under 35 U.S.C. §119 (e) of U.S. Provisional Patent Application Ser. No. 61/474, 115 filed on Apr. 11, 2011, which is incorporated herein by reference.

FIELD

The present invention is directed to the area of implantable electrical stimulation systems and methods of making and using the systems. The present invention is also directed to implantable electrical stimulation paddle leads with systems and methods for assisting placement of the paddle leads within a patient.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a paddle lead assembly for providing electrical stimulation of patient tissue. The paddle lead assembly includes a paddle body; a plurality of electrodes disposed on the paddle body; a plurality of lead bodies coupled to the paddle body; an array of terminals disposed on each of the plurality of lead bodies; and a plurality of conductive wires. Each conductive wire couples one of the electrodes to at least one terminal of at least one of the terminal arrays. The paddle lead assembly further includes an implantation aid configured and arranged to fit over a portion of at least one of the lead bodies to provide additional stiffness proximal to the paddle body for aiding in implantation of the paddle body into a patient.

Another embodiment is an electrical stimulating system that includes the paddle lead assembly described above; at least one control module configured and arranged to electrically couple to each of the electrodes of the paddle lead assembly; and a connector assembly for receiving at least one of the lead bodies. Each of the at least one control module includes a housing and an electronic subassembly disposed in the housing. The connector assembly includes a connector housing, defining a port at a distal end of the connector housing, and a plurality of connector contacts disposed in the connector housing. The port is configured and arranged for receiving a portion of one of the plurality of lead bodies. The connector contacts are configured and arranged to couple to at least one of the plurality of terminals disposed on each of the at least one of the lead bodies.

Yet another embodiment is a method for stimulating tissue. The method includes providing the paddle lead assembly described above with the implantation aid fit over a portion of at least one of the lead bodies and disposed near the paddle body. The method further includes implanting the paddle body of the paddle lead assembly into tissue a patient such that at least some of the electrodes are disposed in proximity to tissue to be stimulated; and providing current to at least some of the electrodes from an electrically coupled pulse generator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads with customizable electrode configurations, as well as methods of making and using the electrodes, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, paddle leads. Examples of electrical stimulation systems with leads are found in, for example, U.S. Pat. Nos. 6,181,969; 6,516,227; 6,609,029; 6,609,032; and 6,741,892; and U.S. Patent Applications Publication Nos. 2003/0114905, 2005/0165465, 2007/0150036; 2007/0161294; 2007/0219595; 2007/0239243; 2007/0150007; and 2008/0071320, and U.S. patent application Ser. No. 11/238,240, all of which are incorporated by reference.

Figure 1:
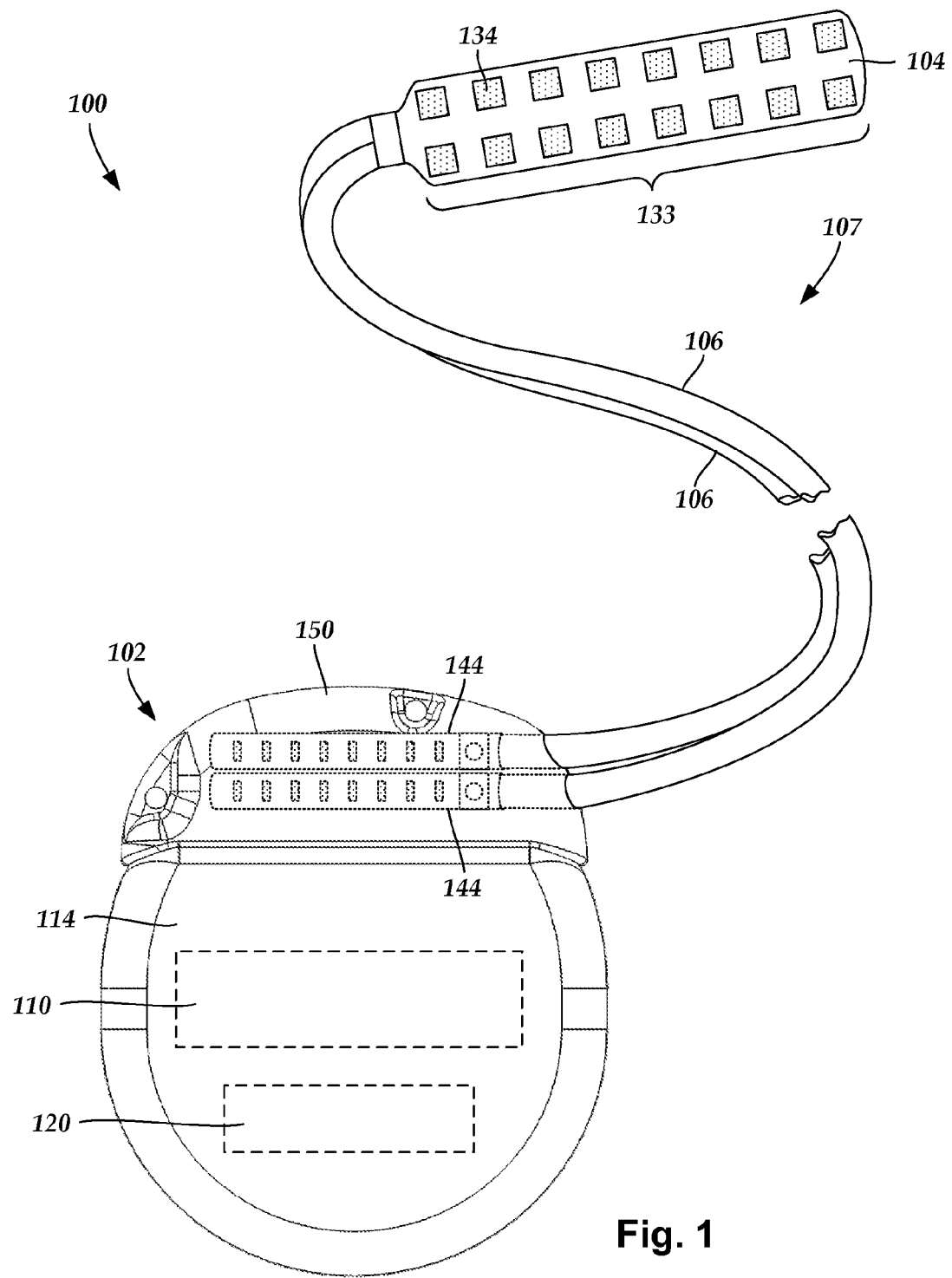
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a paddle lead 107. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 2A) disposed in the connector assembly 144 and terminals (e.g., 310 in FIG. 2A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 2B) can be disposed between the one or more lead bodies 106 and the control module 102 to extend the distance between the one or more lead bodies 106 and the control module 102. It will be understood that the electrical stimulation system can include more, fewer, or different components and can have a variety of different configurations including those configurations disclosed in the electrical stimulation system references cited herein.

The electrical stimulation system or components of the electrical stimulation system, including one or more of the lead bodies 106, the control module 102, and the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 2A) are typically disposed at the proximal end of the one or more lead bodies 106 for connection to corresponding conductive contacts (e.g., 316 in FIG. 2A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 2A) to the electrodes 134. Typically, one or more electrodes 134 are electrically coupled to a terminal (e.g., 310 in FIG. 2A). In some embodiments, each terminal (e.g., 310 in FIG. 2A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 2A:
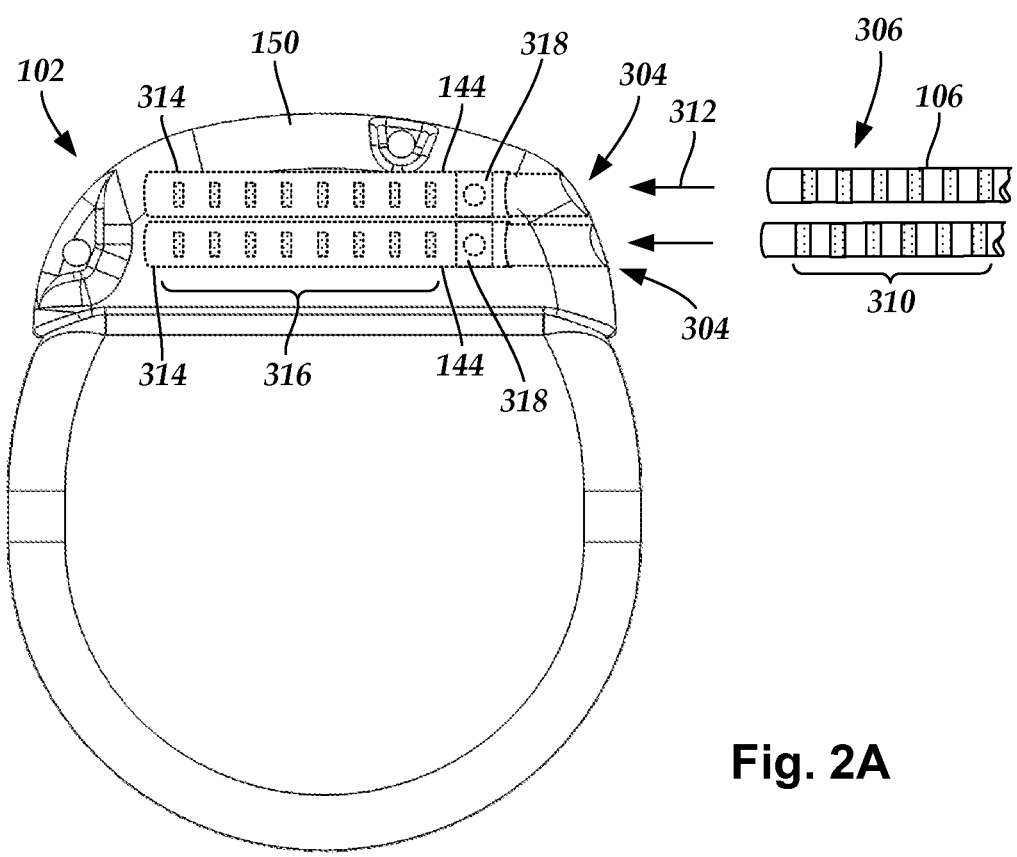
FIG. 2A is a schematic view of one embodiment of the control module of FIG. 1, the connector assemblies configured and arranged to receive the proximal portions of the lead bodies of FIG. 1, according to the invention.

FIG. 2A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 2A, proximal ends 306 of the plurality of lead bodies 106 are shown configured and arranged for insertion to the control module 102.

In FIG. 2A, the one or more connector assemblies 144 are disposed in the header 150. In at least some embodiments, the header 150 defines one or more ports 304 into which the proximal end(s) 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body 106.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. Patent Application Publication No. 2008/0071320, which are incorporated by reference.

Figure 2B:
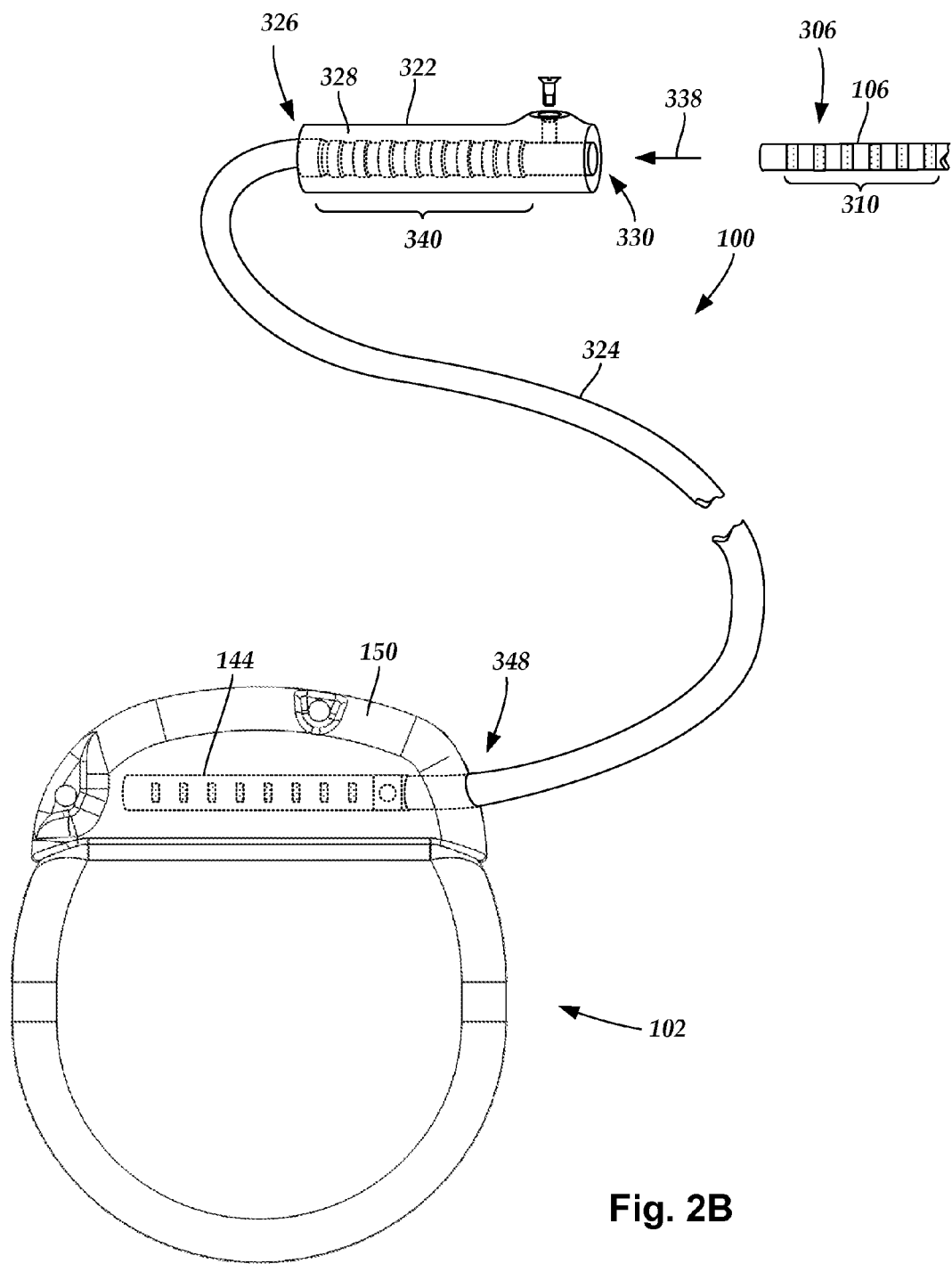
FIG. 2B is a schematic view of one embodiment of a proximal portion of a lead body, a lead extension, and a control module, the lead extension configured and arranged to couple the lead body to the control module, according to the invention.

In at least some embodiments, the electrical stimulation system includes one or more lead extensions. The one or more lead bodies 106 can be coupled to one or more lead extensions which, in turn, are coupled to the control module 102. In FIG. 2B, a lead extension connector assembly 322 is disposed on a lead extension 324. For clarity of illustration, only a single lead extension 326 and single lead body 106 are illustrated, but it will be understood that multiple lead extensions and multiple lead bodies may be used or that a lead extension 326 may include be configured to receive the proximal ends of multiple lead bodies simultaneously.

The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 2B), the proximal end 348 of the lead extension 324 is configured and arranged for insertion into the connector assembly 144 disposed on the control module 102.

It will be understood that the control modules 102 can receive either lead bodies 106 or lead extensions 324. It will also be understood that the electrical stimulation system 100 can include a plurality of lead extensions 224. For example, each of the lead bodies 106 shown in FIGS. 1 and 2A can, alternatively, be coupled to a different lead extension 224 which, in turn, are each coupled to different ports of a two-port control module, such as the control module 102 of FIGS. 1 and 2A.

In the case of paddle leads 107, electrodes 134 can be disposed on the paddle body 104 in any suitable arrangement. For example, in FIG. 1 the electrodes 134 are shown in a configuration that includes rows and columns. In FIG. 1, the paddle body 104 is shown having two electrodes 134 per row and eight electrodes 134 per column, or a "2×8" configuration.

Figure 3:
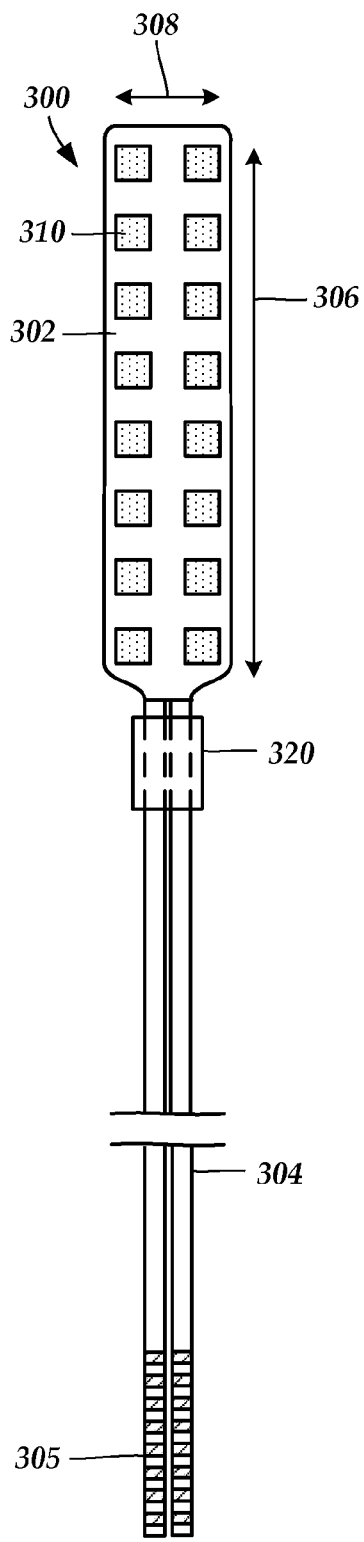
FIG. 3 is a schematic top view of one embodiment of a paddle lead assembly with an implantation aid, according to the invention.

FIG. 3 is a schematic top view of one embodiment of a paddle lead assembly 300. The paddle lead assembly 300 includes a paddle body 302 and a plurality of lead bodies 304. At least some of the plurality of lead bodies 304 include arrays of terminals 305. In at least some embodiments, terminal arrays 305 are disposed on each of the plurality of lead bodies 304.

The paddle body 302 includes a longitudinal axis 306 and a transverse axis 308 that is transverse to the longitudinal axis 306. The paddle body 302 includes an array of electrodes 310. The paddle body 302 can include any number of electrodes in the electrode array including, for example, sixteen, eighteen, twenty, twenty-two, twenty-four, twenty-six, twenty-eight, thirty, thirty-two, thirty-four, or more electrodes. It will be understood that other numbers of electrodes may be used instead.

Individual electrodes 310 within the electrode array may be arranged into columns extending parallel with the longitudinal axis 306 of the paddle body 302. Each of the columns of the electrode array may include the same number of electrodes. In at least some embodiments, at least one of the columns of the electrode array include a different number of electrodes from one or more of the other columns. In FIG. 3, each of the columns of the electrode array is shown having eight electrodes 310. It will be understood that other numbers of electrodes, either fewer or greater, may be disposed in each column. For example, each of the columns can include two, three, four, five, six, seven, eight, nine, ten, eleven, twelve, thirteen, fourteen, fifteen, sixteen, seventeen, eighteen, nineteen, twenty, twenty-four, thirty-two or more electrodes. It will be understood that other regular or irregular arrangements of electrodes 310 on the paddle body 302 can be used.

Each of the electrodes 310 of the electrode array may be independently operated, via a pulse generator disposed in the control module 102. In at least some embodiments, the control module 102 has at least as many independently programmable stimulation channels as electrodes 310 in the electrode array. The control module 102 (FIG. 1) stimulation channels may be independently programmable, preferably to deliver constant current stimulus pulses to each of the electrodes 310 of the electrode array. The constant current stimulus pulses may be biphasic in form.

When the electrical stimulation system has sufficient independently programmable channels in the control module 102 (FIG. 1), each of the electrodes 310 of the array may independently function as a cathode, as an anode, or be effectively turned off at any point in time. When a biphasic cathodic stimulus pulse is delivered through a particular electrode of the electrode array, that particular electrode is referred to as a "cathode." When the same particular electrode is functioning in the opposite polarity (a positive spike followed by longer duration negative return), that particular electrode is referred to as an "anode." The use of the term "cathode" or "anode" as used herein, refers to whether the particular electrode in the paddle body that is delivering a biphasic stimulus pulse is sinking or sourcing the stimulus current.

Each channel of the control module may be programmed to operate as a cathode, an anode, or be turned off at any one time. Additionally, each stimulus channel may sink different magnitudes of stimulus current through two or more cathode electrodes and source stimulus current with different magnitudes through two or more anodes. Moreover, the housing (114 in FIG. 1) of the control module 102 can be programmed to be an anode or to be OFF. The control module 102 may also enable many different configurations of monopolar stimulation (i.e., one or more of the electrodes in the electrode array may concurrently be delivering a cathodic stimulus pulse, while the remainder of the electrodes are OFF and the housing (114 of FIG. 1) of the control module 102 is turned on as the anode).

Additionally, the stimulation system may also enable many different configurations of multipolar stimulation (i.e., one or more of the electrodes in the electrode array may function as cathodes and, concurrently, one or more of the electrodes may function as anodes). Alternatively, it may be possible to have a hybrid stimulation system (i.e., one or more of the electrodes in the electrode array is functioning as an anode and, concurrently, the housing (114 of FIG. 1) of the control module may be functioning as an anode).

One or more conductive wires electrically couple the electrodes 310 to the terminals 305. At least a portion of the conductive wires extend within the lead bodies 304. In at least some embodiments, each electrode 310 is coupled to a single different corresponding terminal 305 on one of the lead bodies 304 via a single conductive wire. In at least some embodiments, at least one conductive wire extends along each of the lead bodies 304.

Any number of lead bodies 304 can be disposed on the paddle lead assembly 300 including, for example, two, three, four, or more lead bodies 706. In FIG. 3, the paddle lead assembly 300 includes two lead bodies 304. In at least some embodiments, the number of lead bodies 304 is equal to the number of columns of electrodes 310.

One particular challenge for the paddle lead assembly is the implantation of the paddle lead assembly. The paddle lead assembly is typically flexible to allow for flexing as the body in which it is implanted moves. This facilitates maintenance of the originally implanted position of the paddle lead assembly and also can reduce damage to surrounding tissues. This desirable flexibility, however, also makes implantation of the paddle lead assembly more difficult because the flexibility of the lead may make insertion of the lead into the desired implantation site challenging.

An implantation aid 320 can be attached or otherwise incorporated into the paddle lead assembly 300 near the paddle body 302 and around a portion of one or more of the lead bodies 304 to impart additional stiffness to the paddle lead assembly, near its distal end, and aid in implantation of the paddle lead assembly. In at least some embodiments, the implantation aid 320 can be used as a push or steer tool to aid in implantation of the paddle body 302.

In at least some embodiments, the implantation aid 320 is removable to permit removal of the implantation aid 320 from the paddle lead assembly 300 after, or during, implantation of the paddle body 302. In some embodiments, the implantation aid 320 may remain disposed on the lead bodies 304 after implantation and may include suture features (described below) to aid in suturing the paddle lead assembly to tissue after implantation. In some embodiments, the implantation aid 320 may be permanently attached to the paddle lead assembly using, for example, sutures, adhesive, and the like.

The implantation aid 320 may be made of any suitable material. Preferably, the implantation aid is made of a biocompatible material, particularly if the implantation aid is to remain implanted with the paddle lead assembly 300. For example, the implantation aid 320 can be made of a polymeric material (for example, silicone, polyurethane, polyetheretherketone, or the like), ceramic, or metal. In some embodiments, the implantation aid 320 can be made of the same polymeric material as the paddle body (for example, silicone or polyurethane) except that the material of the implantation aid has a higher durometer than the material of the paddle body. In at least some embodiments, the material of the implantation aid has a durometer that is at least 20%, 30%, 40%, 50%, 75%, 100%, 150%, or 200% higher than the durometer of the material of the paddle body.

Figure 4:
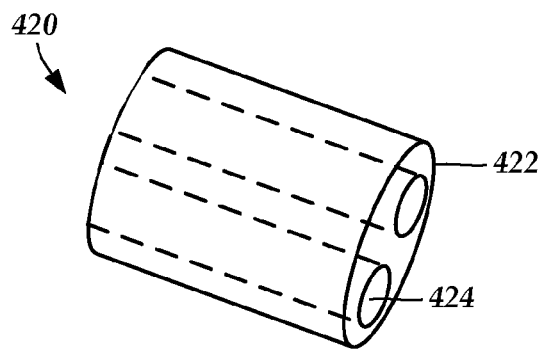
FIG. 4 is a schematic perspective view of one embodiment of an implantation aid, according to the invention.

FIG. 4 illustrates one embodiment of an implantation aid 420. The implantation aid 420 includes an aid body 422 and one or more lumens 424 defined by the aid body 422 and configured to receive one of the lead bodies 304 (FIG. 3) of the paddle lead assembly. The implantation aid may define any number of lumens including one, two, three, four, or more lumens. In at least some embodiments, the number of lumens corresponds to the number of lead bodies of the paddle lead assembly.

In at least some embodiments, the implantation aid 420 can slide onto one or more lead bodies of the paddle lead assembly. In at least some embodiments, the lumens 424 provide a friction fit with the lead bodies of the paddle lead assembly. In other embodiments, the diameter of the lumens 424 is substantially larger than a diameter of the lead bodies.

The aid body 422 may be formed as a single piece or may be formed as two or more individual pieces that are coupled together. For example, the aid body 422 may be formed of two or more pieces that are placed around one or more of the lead bodies and then coupled together (e.g., snapped or adhesively attached together). Although illustrated as a cylinder in FIG. 4, it will be recognized that the aid body 422 can be formed in other regular or irregular shapes.

Figure 5:
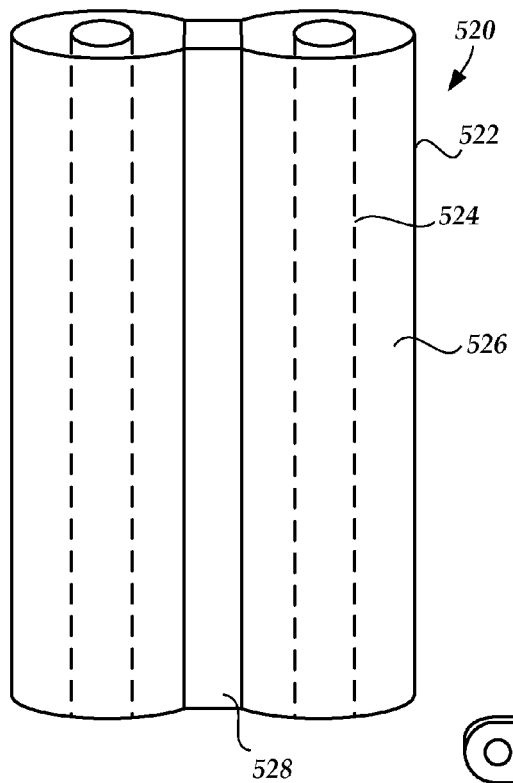
FIG. 5 is a schematic perspective view of a second embodiment of an implantation aid, according to the invention.

FIG. 5 illustrates another embodiment of an implantation aid 520. In this particular embodiment, the aid body 522 is formed from multiple cylindrical portions 526 that are coupled together by one or more connecting portions 528. Each of the cylindrical portions 526 defines at least one lumen 524 configured to receive one of the lead bodies 304 (FIG. 3) of the paddle lead assembly. The implantation aid may define any number of cylindrical portions includes two, three, four, or more cylindrical portions. In at least some embodiments, the number of cylindrical portions and the number of lumens corresponds to the number of lead bodies of the paddle lead assembly. The cylindrical portions can be arranged in any suitable manner including, for example, in a side-by-side arrangement, as illustrated in FIG. 5, or, when there are more than two cylindrical portions, in non-linear arrangements (e.g., arrangements with the cylindrical portions being positioned at points of triangle, rectangle, square, hexagon, and the like when viewed from an end of the implantation aid).

In at least some embodiments, the implantation aid 520 can slide onto one or more lead bodies of the paddle lead assembly. In at least some embodiments, the lumens 524 provide a friction fit with the lead bodies of the paddle lead assembly. In other embodiments, the diameter of the lumens 524 is substantially larger than a diameter of the lead bodies.

The aid body 522 may be formed as a single piece or may be formed as two or more individual pieces that are coupled together. For example, the aid body 522 may be formed of two or more pieces that are placed around one or more of the lead bodies and then coupled together (e.g., snapped or adhesively attached together).

Figure 6:
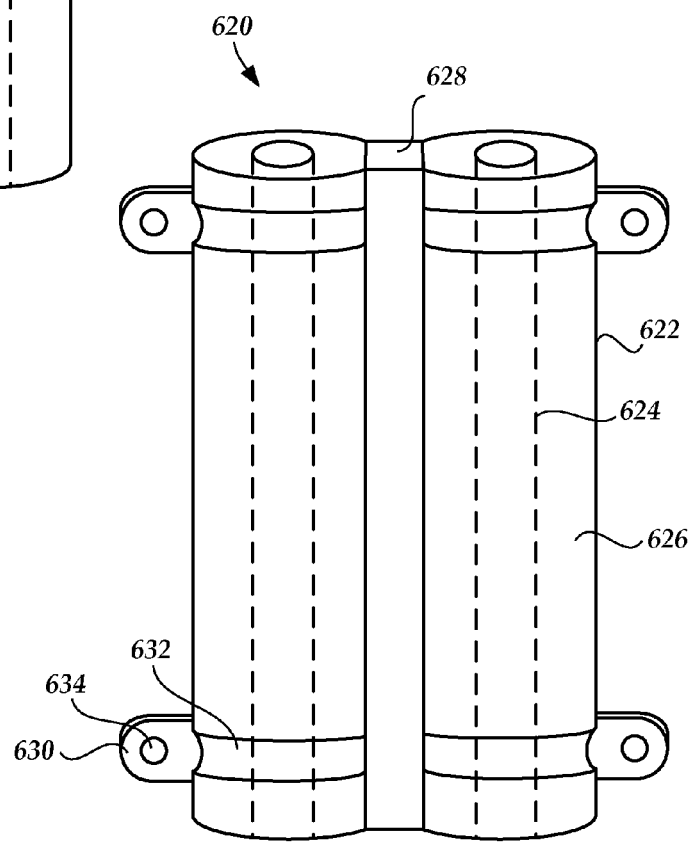
FIG. 6 is a schematic perspective view of a third embodiment of an implantation aid, according to the invention.

FIG. 6 illustrates another embodiment of an implantation aid 620 with an aid body 622, cylindrical portions 626, connecting portion 628, and lumens 624, similar to those of the embodiment of FIG. 5. In addition, the implantation aid 620 includes one or more suture features, such as one or more suture tabs 630, one or more suture grooves 632, or both.

One or more suture tabs 630 can extend from the aid body 622. The suture tabs 630 can be made of the same or a different material from the aid body 622. Each suture tab 630 includes at least one opening 634 through which a suture can pass. If the implantation aid 620 includes more than one suture tab 630 then the suture tabs can be arranged in any suitable configuration. For example, one or more suture tabs 630 may be arranged on opposite sides of the aid body 622, as illustrated in FIG. 6. One or more suture tabs 630 may be arranged near opposite ends of the aid body 622, as illustrated in FIG. 6. In some embodiments, there may be two suture tabs that are on opposite sides and near opposite ends of the aid body.

The aid body 622 may include one or more suture grooves 632 formed in the cylindrical portions 626, as illustrated in FIG. 6. Optionally, the suture grooves may also extend along the connecting portions of the aid body as well. If the implantation aid also includes suture tabs 630, then one or more of the suture grooves may be aligned with the suture tabs 630. Optionally, there may be other suture grooves that are not aligned with the suture tabs. The suture grooves may facilitate maintaining the sutures wrapped around the aid body 622 and prevent or reduce the likelihood that the sutures will slip off the aid body.

It will be recognized that suture tabs, suture grooves, or both may be added to the implantation aid embodiments of FIGS. 4 and 5.

Figure 7:
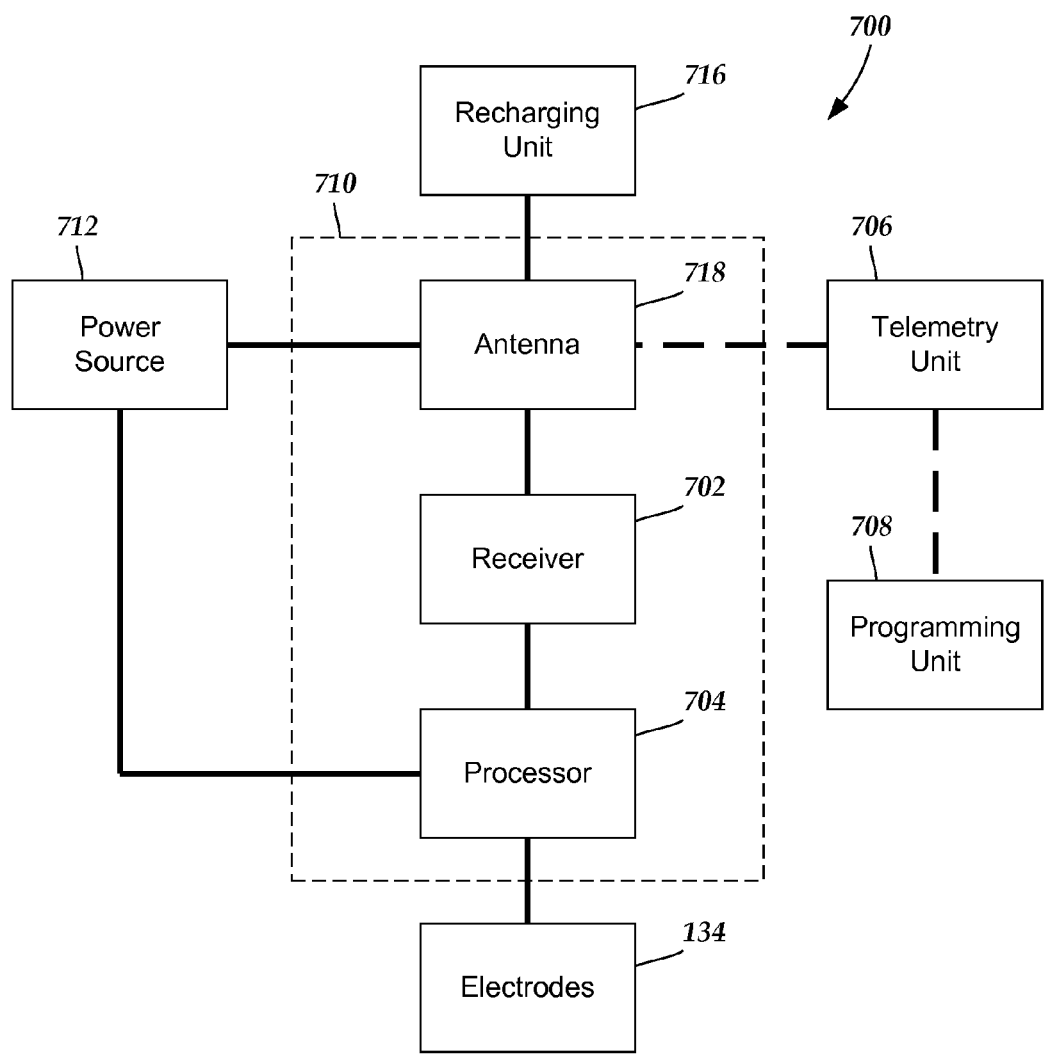
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead assembly for providing electrical stimulation of patient tissue, the paddle lead assembly comprising:
   a paddle body;
   a plurality of electrodes disposed on the paddle body;
   a plurality of lead bodies coupled to the paddle body;
   an array of terminals disposed on each of the plurality of lead bodies;
   a plurality of conductive wires, each conductive wire coupling one of the electrodes to at least one terminal of at least one of the terminal arrays; and
   an implantation aid disposed on a portion of at least two of the lead bodies proximate to the paddle body to provide additional stiffness proximal to the paddle body for aiding in implantation of the paddle body into a patient, wherein the implantation aid is removable from the at least two of the lead bodies and the paddle body, wherein a material of the implantation aid has a higher durometer than a material of the paddle body, wherein the implantation aid defines a plurality of lumens, each lumen configured and arranged for fitting over a portion of one of the lead bodies.

2. An electrical stimulating system comprising:
   the paddle lead assembly of claim 1;
   at least one control module configured and arranged to electrically couple to each of the electrodes, each of the at least one control module comprising
      a housing, and
      an electronic subassembly disposed in the housing; and
   a connector assembly for receiving at least one of the lead bodies, the connector assembly comprising
      a connector housing defining a port at a distal end of the connector housing, the port configured and arranged for receiving a portion of one of the plurality of lead bodies, and
      a plurality of connector contacts disposed in the connector housing, the connector contacts configured and arranged to couple to at least one of the plurality of terminals disposed on each of the at least one of the lead bodies.

3. A method for stimulating tissue, the method comprising:
   providing the paddle lead assembly of claim 1, wherein the implantation aid is fit over a portion of at least one of the lead bodies and disposed proximate to the paddle body to provide additional stiffness proximal to the paddle body for aiding in implantation of the paddle body into a patient;
   implanting the paddle body of the paddle lead assembly into tissue a patient such that at least some of the electrodes are disposed in proximity to tissue to be stimulated; and
   providing current to at least some of the electrodes from an electrically coupled pulse generator.

4. A paddle lead assembly for providing electrical stimulation of patient tissue, the paddle lead assembly comprising:
   a paddle body;
   a plurality of electrodes disposed on the paddle body;
   a plurality of lead bodies coupled to the paddle body;
   an array of terminals disposed on each of the plurality of lead bodies;
   a plurality of conductive wires, each conductive wire coupling one of the electrodes to at least one terminal of at least one of the terminal arrays; and
   an implantation aid disposed on a portion of at least two of the lead bodies proximate to the paddle body to provide additional stiffness proximal to the paddle body for aiding in implantation of the paddle body into a patient, wherein the implantation aid is removable from the at least two of the lead bodies and the paddle body and the implantation aid comprises at least one of the suture feature for suturing the implantation aid to tissue of the patient, wherein the implantation aid defines a plurality of lumens, each lumen configured and arranged for fitting over a portion of one of the lead bodies.

5. The paddle lead assembly of claim 4, wherein the implantation aid comprises an aid body, the aid body comprising a plurality of cylindrical portions and at least one connecting portion, wherein the at least one connecting portion couples the plurality of cylindrical portions together, each of the cylindrical portions defining at least one of the lumens.

6. The paddle lead assembly of claim 4, wherein the implantation aid comprises an aid body and the at least one suture feature comprises at least one suture tab extending from the aid body.

7. The paddle lead assembly of claim 6, wherein the at least one suture tab comprises a first suture tab and a second suture tab, wherein the first and second suture tabs extend from opposite sides of the aid body and from near opposite ends of the aid body.

8. The paddle lead assembly of claim 6, wherein the at least one suture feature further compromises at least one suture groove formed in an exterior of the aid body.

9. The paddle lead assembly of claim 4, wherein the implantation aid comprises an aid body and the at least one suture feature comprises at least one suture groove formed in an exterior of the aid body.

10. The paddle lead assembly of claim 4, wherein the implantation aid is slidable over the lead bodies.

11. The paddle lead assembly of claim 4, wherein the implantation aid and paddle body are both made of silicone or both made of polyurethane.

12. The paddle lead assembly of claim 4, wherein the implantation aid is cylindrical.

13. An electrical stimulating system comprising:
   the paddle lead assembly of claim 4;
   at least one control module configured and arranged to electrically couple to each of the electrodes, each of the at least one control module comprising
      a housing, and
      an electronic subassembly disposed in the housing; and
   a connector assembly for receiving at least one of the lead bodies, the connector assembly comprising
      a connector housing defining a port at a distal end of the connector housing, the port configured and arranged for receiving a portion of one of the plurality of lead bodies, and
      a plurality of connector contacts disposed in the connector housing, the connector contacts configured and arranged to couple to at least one of the plurality of terminals disposed on each of the at least one of the lead bodies.

14. The electrical stimulating system of claim 13, wherein the Connector assembly is disposed on the control module.

15. The electrical stimulating system of claim 13, further including a lead extension having a distal end and at least one proximal end, the connector assembly disposed on the distal end of the lead extension.

16. The electrical stimulating system of claim 15, wherein at least one of the proximal ends of the lead extension is configured and arranged for insertion into another connector.

17. A method for stimulating tissue, the method comprising:
   providing the paddle lead assembly of claim 4, wherein the implantation aid is fit over a portion of at least one of the lead bodies and disposed proximate to the paddle body to provide additional stiffness proximal to the paddle body for aiding in implantation of the paddle body into a patient;
   implanting the paddle body of the paddle lead assembly into tissue a patient such that at least some of the electrodes are disposed in proximity to tissue to be stimulated; and
   providing current to at least some of the electrodes from an electrically coupled pulse generator.

18. The method of claim 17, further comprising suturing the paddle lead assembly to the tissue of the patient with sutures disposed, at least in part, around the implantation aid.

19. A paddle lead assembly for providing electrical stimulation of patient tissue, the paddle lead assembly comprising:
   a paddle body;
   a plurality of electrodes disposed on the paddle body;
   a plurality of lead bodies coupled to the paddle body;
   an array of terminals disposed on each of the plurality of lead bodies;
   a plurality of conductive wires, each conductive wire coupling one of the electrodes to at least one terminal of at least one of the terminal arrays; and
   an implantation aid disposed on a portion of at least two of the lead bodies proximate to the paddle body to provide additional stiffness proximal to the paddle body for aiding in implantation of the paddle body into a patient, wherein the implantation aid is removable from the at least two of the lead bodies and the paddle body and the implantation aid comprises an aid body and at least one suture tab extending from the aid body for suturing the implantation aid to tissue of the patient, wherein the at least one suture tab comprises a first suture tab and a second suture tab, wherein the first and second suture tabs extend from opposite sides of the aid body and from near opposite ends of the aid body.

* * * * *